(12) United States Patent
Kraft

(10) Patent No.: US 8,153,848 B2
(45) Date of Patent: Apr. 10, 2012

(54) HOMOALLYL ALCOHOLS USEFUL AS FRAGRANCES

(75) Inventor: Philip Kraft, Duebendorf (CH)

(73) Assignee: Givaudan SA, Vernier (CH)

( * ) Notice: Subject to any disclaimer, the term of this patent is extended or adjusted under 35 U.S.C. 154(b) by 136 days.

(21) Appl. No.: 12/743,096

(22) PCT Filed: Nov. 20, 2008

(86) PCT No.: PCT/CH2008/000493
§ 371 (c)(1), (2), (4) Date: May 14, 2010

(87) PCT Pub. No.: WO2009/065244
PCT Pub. Date: May 28, 2009

(65) Prior Publication Data
US 2011/0130470 A1 Jun. 2, 2011

(30) Foreign Application Priority Data

Nov. 22, 2007 (GB) .................................. 0722824.0

(51) Int. Cl.
*C07C 33/25* (2006.01)
*A61K 8/34* (2006.01)
(52) U.S. Cl. .................. 568/909.5; 514/739; 512/25
(58) Field of Classification Search ............. 568/909.5; 514/739; 512/25
See application file for complete search history.

(56) References Cited

U.S. PATENT DOCUMENTS 4,336,164 A * 6/1982 Boden .............................. 512/25
4,480,646 A * 11/1984 Boden ........................... 131/276

FOREIGN PATENT DOCUMENTS

| EP | 0003361 A1 | 8/1979 |
| EP | 0269999 A | 6/1988 |
| EP | 0365996 A | 5/1990 |
| GB | 1167776 A | 10/1969 |
| JP | 53044505 A | 4/1978 |

* cited by examiner

*Primary Examiner* — Sikarl Witherspoon
(74) *Attorney, Agent, or Firm* — Norris McLaughlin & Marcus PA

(57) ABSTRACT

Branched, highly-substituted $C_9$-$C_{13}$ homoallyl alcohols of formula I,

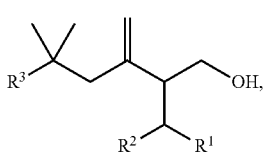

in which $R^1$ and $R^2$ are selected from H or Me and $R^3$ is selected from H, Me and Et.

The compounds are useful in fragrance applications in which a floral note is desired.

6 Claims, No Drawings

HOMOALLYL ALCOHOLS USEFUL AS FRAGRANCES

This is an application filed under 35 USC 371 of PCT/CH2008/000493.

This invention relates to novel odoriferous homoallyl alcohols, more specifically 2,5,5-trialkyl-3-methylenehexan-1-ols, which possess new green-floral odours, and to the use of these perfumery materials in fragrance applications.

Floral bouquets have always been eagerly sought in the fragrance field, and many examples have been prepared and commercialised. Particularly desirable are rose notes that possess green-herbaceous side notes or dry almost earthy-woody characters, to give odorants with reduced sweetness that appear and smell more natural.

It has now been found that 2,5-dialkyl-5-methyl-3-methylenehexan-1-ols constitute a new, well-defined class of odorants situated between rose, hyacinth and lilac, and that these possess these highly-desirable facets that reduce the stereotypical sweetness of rose odorants and incorporate new natural side notes ranging from green-herbaceous to earthy-woody.

There is therefore provided a compound of the formula I,

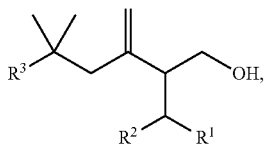

I in which $R^1$ and $R^2$ are selected from H or Me and $R^3$ is selected from H, Me and Et.

The compounds of formula I may be used singly, or in combinations of two or more such compounds.

Particularly preferred compounds of formula I are 2,5-dimethyl-3-methylenehexan-1-ol, 2,5,5-trimethyl-3-methylenehexan-1-ol, 2-ethyl-5-methyl-3-methylenehexan-1-ol, 2-ethyl-5,5-dimethyl-3-methylenehexan-1-ol, 2-isopropyl-5-methyl-3-methylenehexan-1-ol and 2-isopropyl-5,5-dimethyl-3-methylenehexan-1-ol.

Depending on the natures of the substituents $R^1$ and $R^2$, the compounds of the present invention comprise one or two chiral centres, and as such exist as racemic or enantiomerically-enriched mixtures of enantiomers. Resolving stereoisomers or employing chiral starting materials adds to the cost of these odorants, so it is preferred to use the compounds as racemic mixtures simply for economic reasons. However, if it is desired to prepare individual stereoisomers, this may be achieved according to methods well known in the art, e.g. preparative HPLC and GC or by stereoselective syntheses, or starting from available chiral raw materials.

The compounds of the formula I may be used alone or in admixture with other fragrances. Preferably they are admixed with other fragrance raw materials. The use of a compound of formula I is not limited to any particular perfume type or to any special olfactory direction, odorant or class of substance. Thus, compounds of the general formula may, for example, be mixed with:

Ethereal oils and extracts, e.g. bergamot oil, coriander oil, galbanum oil, geranium oil, jasmin absolute, lemon oil, lime oil, neroli oil, oak moss absolute, patchouli oil, petitgrain oil, rose oil, sandalwood oil or ylang-ylang oil;

Alcohols, e.g. citronellol, dihydromyrcenol, Ebanol®, eugenol, geraniol, linalool, phenylethyl alcohol, Sandalore®, Super Muguet®, terpineol or Timberol®;

Aldehydes and ketones, e.g. α-amylcinnamaldehyde, decanal, Hedione®, hydroxycitronellal, isoeugenol, Iso E Super®, Isoraldeine®, methyl ionone or vanillin;

Ether and acetals, e.g. Ambrofix®, geranyl methyl ether, Magnolan®, rose oxide or Spirambrene®

Esters and lactones, e.g. ambrettolide, benzyl acetate, benzyl salicylate, coumarin, γ-decalactone, ethylene brassylate, Serenolide®, Thibetolide®, γ-undecalactone or vetivenyl acetate;

Heterocycles, e.g. galbazine, indol, isobutylchinoline.

Due to their unique green-floral rosy character, the compounds of formula I are especially well suited for use in floral feminine fine fragrances, or in compositions for laundry- or home-care applications.

In addition to their admixture with other fragrances, the compounds of the present invention may be admixed with one or more ingredients or excipients conventionally used in conjunction with fragrances in perfume compositions, for example carrier materials, and other auxiliary agents commonly used in the art, e.g., solvents such as dipropylene glycol (DPG), isopropyl myristate (IPM), and triethyl citrate (TEC).

The compounds of the present invention may be used in a broad range of fragrance applications, e.g. in any field of fine and functional perfumery, such as perfumes, household products, laundry products, body care products and cosmetics. The compounds may be employed in widely varying amounts, depending upon the specific application and on the nature and quantity of other fragrances. The proportions in which the compounds of the present invention are employed in application may vary within a large range of values and will depend upon the nature of the applications one intends to perfume, for example the nature of co-ingredients, and the particular effect that the perfumer seeks. Generally however, one may employ up to about 10% by weight in fine fragrances, e.g. from about 0.5% by weight to about 5% by weight, and up to about 20% by weight based on the perfume composition in other fragrance applications, e.g. laundry products. However, these values are given only by way of example, since the experienced perfumer may also achieve effects or may create novel accords with lower or higher concentrations.

The compounds of the present invention may be employed into the fragrance application simply by directly mixing the perfume composition with the fragrance application, or they may, in an earlier step, be entrapped with an entrapment material such as polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzymes, or the like, and then mixed with the application.

Thus, there is additionally provided a method of manufacturing a fragrance application and consumer products resulting therefrom, comprising the incorporation therein of a compound of formula I as a fragrance ingredient, either by directly admixing the compound to the application or by admixing a perfume composition comprising a compound of formula I, which may then be mixed to a fragrance application, using conventional techniques and methods. Through the addition of an olfactory acceptable amount of a compound of the present invention, or a mixture thereof, the odour notes of a fragrance application will be improved, enhanced or modified.

There is also provided a method for improving, enhancing or modifying a fragrance application, comprising the addition thereto of an olfactorily-acceptable amount of a compound of formula I, or a mixture thereof.

There is further provided a fragrance application comprising:

a) as odorant a compound of formula I or a mixture thereof; and b) a consumer product base.

As used herein, 'fragrance application' includes any products, such as fine fragrances, e.g. eaux de perfume and eaux de toilette; household products, e.g. detergents for dishwasher, surface cleaner, air freshener; laundry products, e.g. softener, bleach, detergent; body care products, e.g. after-shave lotion, shampoo, shower gel, shower and bath salt, hygiene product; and cosmetics, e.g. deodorants, vanishing creams, comprising an odorant. This list of products is given by way of illustration and is not to be regarded as being in any way limiting.

The compounds of formula I may conveniently be prepared by Wittig-Horner-Emmons reaction of 4-methylpentan-2-one or 4-alkyl-4-methylpentan-2-one with ethyl 2-(diethoxyphosphoryl)acetate, as described in, for example, P. Kraft, W. Eichenberger, Eur. J. Org. Chem. 2004, 334-365, followed by deconjugative alkylation of the formed α,β-unsaturated ethyl ester with lithium diisopropyl amide (LDA) and a suitable halogen alkane, as described in, for example, R. M. Cory, B. M. Ritchie, A. M. Shrier, Tetrahedron Lett. 1990, 31, 6789-6792. Reduction of the resulting β,γ-unsaturated ester, for instance with lithium aluminium hydride (LAH), then provides the homoallyl alcohols of formula I.

The invention is now further described with reference to the following non-limiting examples. These examples are for the purpose of illustration only and it is understood that a person skilled in the art can make variations and modifications. The NMR data are given relative to internal SiMe$_4$ standard.

EXAMPLE 1

2,5-Dimethyl-3-methylenehexan-1-ol

To a stirred suspension of sodium hydride (55% in mineral oil, 43.6 g. 1.00 mol) in THF (200 mL) was added dropwise at room temp. ethyl 2-(diethoxyphosphoryl)acetate (224 g, 1.00 mol) in THF (800 mL), and the reaction mixture was refluxed for 1 h. The reaction mixture was allowed to cool to room temp., and 4-methylpent-2-one (100 g, 1.00 mol) in THF (300 mL) was added dropwise over a period of 45 min. The reaction mixture was refluxed overnight, quenched with satd. aq. NH$_4$Cl solution (700 mL) and extracted with Et$_2$O (3×500 mL). The combined organic extracts were dried (Na$_2$SO$_4$), and concentrated under reduced pressure. The resulting residue was purified by distillation over a 20-cm Vigreux column to furnish at 72-74° C./2 mbar (E/Z)-ethyl 3,5-dimethylhex-2-enoate (119 g, 70%) as a mixture of isomers (E/Z=7:3). IR (neat): ν=1731/1645 (s, ν C=O), 1464 (w, δ$_{as}$ CH$_3$), 1367 (w, δ$_s$ CH$_3$), 1144 (s, ν C—O) cm$^{-1}$. $^1$H NMR (CDCl$_3$): δ=0.89/0.93 (2d, J=6.5 Hz, 6H, 5-Me$_2$), 1.25/1.27 (2t, J=7.5 Hz, 3H, 2'-H$_3$), 1.87 (m, 1H, 5-H), 1.99 (d, J=7.0 Hz, 2H, 4-H$_2$), 2.13/2.14 (2s, 3H, 3-Me), 4.13/4.14 (2q, J=7.5 Hz, 2H, 1'-H$_2$), 5.63/5.64 (2s, 1H, 2-H) ppm. $^{13}$C NMR (CDCl$_3$): δ=14.1/14.2 (2q, 2'-C), 16.1/18.4 (2q, 3-Me), 22.3/25.3 (2q, 5-Me$_2$), 26.1/27.2 (2d, C-5), 41.5/50.4 (2t, C-4), 59.1/59.2 (2t, C-1'), 116.6/117.1 (2d, C-2), 158.9/159.2 (2s, C-3), 166.3/166.6 (2s, C-1) ppm. MS (EI): m/z (%)=170 (25) [M$^+$], 155 (16) [M$^+$-CH$_3$], 127 (32) [M$^+$-C$_3$H$_7$], 125 (86) [M$^+$-C$_2$H$_5$O], 100 (100) [C$_5$H$_8$O$_2^+$], 43 (80) [C$_3$H$_7^+$]. Odour description: Interesting, fruity note reminiscent of wine with additional anisic facets, and even slightly sweaty and woody aspects.

A solution of N,N'-dimethylpropyleneurea (DMPU, 40.4 g, 315 mmol) in THF (300 mL) was added at −70° C. within 30 min to a stirred solution of lithium diisopropylamide (LDA, 2 M in THF, 157 mL, 315 mmol). After 10 min of stiffing at −70° C., a solution of (E/Z)-ethyl 3,5-dimethylhex-2-enoate (35.7 g, 210 mmol) in THF (300 mL) was added over a period of 45 min The reaction mixture was allowed to warm to −20° C., treated dropwise with iodomethane (44.7 g, 315 mmol), and stirred overnight at room temp. Then, satd. aq. NH$_4$Cl solution (600 mL) was added dropwise, and the reaction mixture was extracted with Et$_2$O (3×400 mL). The combined organic extracts were dried with Na$_2$SO$_4$, and evaporated on a rotary evaporator. The resulting residue was purified by silica-gel flash chromatography (pentane/Et$_2$O, 98:2, R$_f$=0.18) to furnish the ethyl 2,5-dimethyl-3-methylenehexanoate (23.2 g, 60%) as a colourless liquid. Odour description: fruity-floral-green note with fruity, green, acidic accents and agrestic undertones.

To a stirred suspension of lithium aluminium hydride (LAH, 4.63 g, 122 mmol) in THF (100 mL) was added dropwise between 3-5° C. within a period of 1 h a solution of ethyl 2,5-dimethyl-3-methylenehexanoate (22.5 g, 122 mmol) in THF (500 mL), and the resulting reaction mixture was stirred for 3 h under reflux. With cooling in an ice-bath, water (5.00 mL) was added dropwise, followed by 15% aq. NaOH solution (5.00 mL) and again water (15.0 mL). After stirring for further 30 min at room temp, the formed precipitate was filtered off by suction with the aid of a sintered funnel, and washed with Et$_2$O (100 mL). The combined filtrates were evaporated under reduced pressure, and the resulting residue was purified by silica-gel flash chromatography (pentane/Et$_2$O, 8:2, R$_f$=0.18) to provide 2,5-dimethyl-3-methylenehexan-1-ol (13.6 g, 79%) as a colourless odoriferous liquid. IR (neat): ν=3332 (s, ν O—H), 1462 (w, δ$_a$, CH$_3$), 1366 (w, δ$_s$, CH$_3$), 1026 (s, ν C—O), 891 (s, δ C=H) cm$^{-1}$. $^1$H NMR (CDCl$_3$): δ=0.90 (d, J=6.5 Hz, 6H, 5-Me$_2$), 1.05 (d, J=7.0 Hz, 3H, 2-Me), 1.69 (br. s, 1H, OH), 1.79 (sept, J=7.0 Hz, 1H, 5-H), 1.91 (dd, J=7.0, 1.5 Hz, 2H, 4-H$_2$), 2.32 (sext, J=6.5 Hz, 1H, 2-H), 3.45-3.59 (m, 2H, 1-H$_2$), 4.86 (d, J=1.5 Hz, 1H, 1'-H$_E$), 4.87 (d, J=1.5 Hz, 1H, 1'-H$_Z$) ppm. $^{13}$C NMR (CDCl$_3$): δ=16.4 (q, 2-Me), 22.3/22.6 (2q, 5-Me$_2$), 26.2 (d, C-5), 41.6 (d, C-2) 44.8 (t, C-4), 65.9 (t, C-1), 110.7 (d, C-1'), 150.1 (s, C-3) ppm. MS (EI): m/z (%)=142 (5) [M$^+$], 124 (3) [M$^+$-CH$_3$], 111 (28) [M$^+$-CH$_3$O], 83 (86) [C$_6$H$_{11}^+$], 69 (100) [C$_5$H$_9^+$]. Odour description: very pleasant and fresh green-rosy note with natural slightly agrestic-earthy aspects and "vert de lilas"-like facets of lilac, hyacinth and peony.

EXAMPLE 2

2,5,5-Trimethyl-3-methylenehexan-1-ol

As described for the preparation of (E/Z)-ethyl 3,5-dimethylhex-2-enoate (vide supra), from 4,4-dimethylpentan-2-one (65.0 g, 569 mmol), sodium hydride (55% in mineral oil, 24.8 g, 569 mmol) and ethyl 2-(diethoxyphosphoryl)acetate (127 g, 569 mmol) in THF (900 mL), (E/Z)-ethyl 3,5,5-trimethylhex-2-enoate (E/Z=7:3, 65.6 g, 63%) was obtained as a colourless liquid after standard work up and purification by distillation over a 20-cm Vigreux column at 78-80° C./2 mbar. IR (neat): ν=1715/1638 (s, ν C=O), 1465 (w, δ$_{as}$ CH$_3$), 1367 (w, $\delta_s$ CH$_3$), 1141 (s, $\nu$ C—O). $^1$H NMR (CDCl$_3$): $\delta$=0.94/0.95 (2s, 9H, 5-Me$_3$), 1.26/1.28 (2t, J=7.0 Hz, 3H, 2'-H$_3$), 1.92/2.06 (2s, 2H, 4-H$_2$), 2.19/2.20 (2s, 3H, 3-Me), 4.13/4.14 (2q, J=7.0 Hz, 2H, 1'-H$_2$), 5.58/5.74 (2s, 1H, 2-H) ppm. $^{13}$C NMR (CDCl$_3$): $\delta$=14.3 (q, 2'-C), 21.8 (q, 3-Me), 30.0/30.3 (2q, 5-Me$_3$), 32.1/32.8 (2s, C-5), 54.7 (t, C-4), 59.4 (t, C-1'), 118.6 (d, C-2), 158.4 (s, C-3), 166.6 (s, C-1) ppm. MS (EI): m/z (%)=184 (3) [M$^+$], 169 (5) [M$^+$-CH$_3$], 139 (19) [M$^+$-C$_2$H$_5$O], 128 (82) [C$_7$H$_{12}$O$_2^+$], 57 (100) [C$_4$H$_9^+$]. Odour description: fruity-green, food-like note with floral, fatty-balsamic and cinnamic aspects.

As described for the preparation of ethyl 2,5-dimethyl-3-methylenehexanoate (vide supra), from (E/Z)-ethyl 3,5,5-trimethylhex-2-enoate (11.8 g, 64.0 mmol) and an LDA solution (2 M in THF, 48.0 mL, 96.0 mmol), DMPU (12.3 g, 96.0 mmol) and 2-iodomethane (18.2 g, 128 mmol) in THF (200 mL), ethyl 2,5,5-trimethyl-3-methylenehexanoate (9.39 g, 74%) was obtained as a colourless liquid after standard workup and purification by silica-gel flash chromatography (pentane/Et$_2$O, 98:2, R$_f$=0.19). Odour description: fruity, wine-like note with floral, buttery and peachy accents and a slight tea connotation.

As described for the preparation of 2,5-dimethyl-3-methylenehexan-1-ol (vide supra), from ethyl 2,5,5-trimethyl-3-methylenehexanoate (8.33 g, 42.0 mmol) and LAH (1.60 g, 42.0 mmol) in THF (250 mL), 2,5,5-trimethyl-3-methylenehexan-1-ol (5.71 g, 87%) was obtained as a colourless odoriferous liquid after standard workup and purification by silica-gel flash chromatography (pentane/Et$_2$O, 8:2, R$_f$=0.20). IR (neat): $\nu$=3327 (s, $\nu$ O—H), 1465 (w, $\delta_{as}$ CH$_3$), 1363 (w, $\delta_s$, CH$_3$), 1025 (s, $\nu$ C—O), 896 (s, $\delta$ C=H) cm$^{-1}$. $^1$H NMR (CDCl$_3$): $\delta$=0.92 (s, 9H, 5-Me$_3$), 1.07 (d, J=7.0 Hz, 3H, 2-Me), 1.69 (br. s, 1H, OH), 1.96 (dd, J=12.0, 1.5 Hz, 1H, 4-H$_a$), 1.97 (dd, J=12.0, 1.0 Hz, 1H, 4-H$_b$), 2.33 (sext, J=6.0 Hz, 1H, 2-H), 3.46 (dd, J=6.0, 6.0 Hz, 1H, 1-H$_a$), 3.48 (dd, J=6.0, 6.0 Hz, 1H, 1-H$_b$), 4.88 (d, J=1.5 Hz, 1H, 1'-H$_E$), 4.92 (d, J=1.5 Hz, 1H, 1'-Hz) ppm. $^{13}$C NMR (CDCl$_3$): $\delta$=16.4 (q, 2-Me), 29.8 (q, 5-Me$_3$), 31.7 (s, C-5), 42.5 (d, C-2) 49.8 (t, C-4), 66.2 (t, C-1), 112.2 (d, C-1'), 149.7 (s, C-3) ppm. MS (EI): m/z (%)=156 (3) [M$^+$], 138 (3) [M$^+$-H$_2$O], 83 (10) [C$_6$H$_{11}^+$], 57 (100) [C$_4$H$_9^+$]. Odour description: pleasant and fresh green-floral note in the direction of hyacinth and rose, with a honey aspect and an agrestic caryophyllene-like inflection.

EXAMPLE 3

2-Ethyl-5-methyl-3-methylenehexan-1-ol

As described for the preparation of ethyl 2,5-dimethyl-3-methylenehexanoate (vide supra), from (E/Z)-ethyl 3,5-dimethylhex-2-enoate (36.3 g, 213 mmol) and an LDA solution (2 M in THF, 160 mL, 320 mmol), DMPU (41.0 g, 320 mmol) and iodoethane (66.5 g, 426 mmol) in THF (700 mL), ethyl 2-ethyl-5-methyl-3-methylenehexanoate (27.9 g, 66%) was obtained as a colourless liquid after standard workup and purification by silica-gel flash chromatography (pentane/Et$_2$O, 98:2, R$_f$=0.17). Odour description: green, fruity-floral note.

As described for preparation of 2,5-dimethyl-3-methylenehexan-1-ol (vide supra), from ethyl 2-ethyl-5-methyl-3-methylenehexanoate (26.8 g, 135 mmol) and LAH (5.12 g, 135 mmol) in THF (500 mL) the 2-ethyl-5-methyl-3-methylenehexan-1-ol (17.5 g, 83%) was obtained as a colourless odoriferous liquid after standard workup and purification by silica-gel flash chromatography (pentane/Et$_2$O, 8:2, R$_f$=0.18). IR (neat): $\nu$=3332 (s, $\nu$ O—H), 1463 (w, $\delta_{as}$ CH$_3$), 1365 (w, $\delta_s$, CH$_3$), 1034 (s, $\nu$ C—O), 892 (s, $\delta$ C=H) cm$^{-1}$. $^1$H NMR (CDCl$_3$): $\delta$=0.88 (t, J=7.5 Hz, 3H, 2'-CH$_3$), 0.91 (d, J=6.5 Hz, 6H, 5-Me$_2$), 1.38-1.49 (m, 2H, 1'-H$_2$), 1.77 (br. s, 1H, OH), 1.78-1.83 (m, 1H, 5-H), 1.85-1.89 (m, 2H, 4-H$_2$), 2.11 (quint, J=8.0 Hz, 1H, 2-H), 3.51-3.55 (m, 2H, 1-H$_2$), 4.86 (d, J=1.5 Hz, 1H, 1'-H$_E$), 4.92 (d, J=1.5 Hz, 1H, 1'-H$_Z$) ppm. $^{13}$C NMR (CDCl$_3$): $\delta$=11.7 (q, C-2'), 22.4/22.7 (2q, 5-Me$_2$), 22.9 (t, C-1'), 25.8 (d, C-5), 44.5 (t, C-4), 49.7 (d, C-2), 64.2 (t, C-1), 111.7 (d, C-1''), 148.3 (s, C-3) ppm. MS (EI): m/z (%)=156 (3) [M$^+$], 142 (2) [M$^+$-CH$_3$], 125 (7) [M$^+$-CH$_3$O], 83 (100) [C$_6$H$_{11}^+$], 69 (100) [C$_5$H$_9^+$], 43 (31) [C$_3$H$_7^+$]. Odour description: pleasant and fresh green-floral note with spicy undertones and a natural agrestic aspects, somewhat reminiscent of beetroot with a slightly earthy twist.

EXAMPLE 4

2-Ethyl-5,5-dimethyl-3-methylenehexan-1-ol

As described for preparation of ethyl 2,5-dimethyl-3-methylenehexanoate (vide supra), from (E/Z)-ethyl 3,5,5-trimethylhex-2-enoate (11.9 g, 62.0 mmol) and an LDA solution (2 M in THF, 46.5 mL, 93.0 mmol), DMPU (11.4 g, 93.0 mmol) and 2-iodoethane (19.4 g, 124 mmol) in THF (250 mL), ethyl 2-ethyl-5,5-dimethyl-3-methylenehexanoate (9.35 g, 71%) was obtained as a colourless liquid after standard workup and purification by silica-gel flash chromatography (pentane/Et$_2$O, 98:2, R$_f$=0.19). Odour descriptions: fruity-floral note in the direction of rose.

As described for preparation of 2,5-dimethyl-3-methylenehexan-1-ol (vide supra), from 7 (8.49 g, 40.0 mmol) and LAH (1.52 g, 40.0 mmol) in THF (250 mL), 2-ethyl-5,5-dimethyl-3-methylenehexan-1-ol (6.07 g, 89%) was obtained as a colourless odoriferous liquid after standard workup and purification by silica-gel flash chromatography (pentane/Et$_2$O, 8:2, R$_f$=0.19; IR (neat): $\nu$=3329 (s, $\nu$ O—H), 1466 (w, $\delta_{as}$CH$_3$), 1363 (w, $\delta_s$ CH$_3$), 1034 (s, $\nu$ C—O), 895 (s, $\delta$ C=H) cm$^{-1}$. $^1$H NMR (CDCl$_3$): $\delta$=0.92 (t, J=7.5 Hz, 3H, 2'-CH$_3$), 0.94 (s, 9H, 5-Me$_3$) 147-154 (m, 2H, 1'-H$_2$), 1.56 (br. s, 1H, OH), 1.95 (dd, J=12.0, 1.5 Hz, 1H, 4-H$_a$), 1.96 (dd, J=12.0, 1.0 Hz, 1H, 4-H$_b$), 2.15 (quint, J=6.0 Hz, 1H, 2-H), 3.52 (dd, J=6.0, 6.0 Hz, 1H, 1-H$_a$), 3.62 (dd, J=6.0, 6.0 Hz, 1H, 1-H$_b$), 4.90 (d, J=1.5 Hz, 1H, 1'-H$_E$), 4.94 (d, J=1.5 Hz, 1H, 1'-H$_Z$) ppm. $^{13}$C NMR (CDCl$_3$): $\delta$=11.9 (q, C-2'), 23.3 (t, C-1'), 29.9 (q, 5-Me$_3$), 31.8 (s, C-5), 49.7 (d, C-2) 50.0 (t, C-4), 63.7 (t, C-1), 112.9 (d, C-1''), 148.2 (s, C-3) ppm. MS (EI): m/z (%)=170 (2) [M$^+$], 152 (2) [M$^+$-H$_2$O], 83 (7) [C$_6$H$_{11}^+$], 57 (100) [C$_4$H$_9^+$]. Odour description: green-floral musty note with natural agrestic and damascone-like aspects and fruity, wine-like undertones and chocolate-type facets.

EXAMPLE 5

2-Isopropyl-5-methyl-3-methylenehexan-1-ol

As described for the preparation of ethyl 2,5-dimethyl-3-methylenehexanoate (vide supra), from (E/Z)-ethyl 3,5-dimethylhex-2-enoate (36.3 g, 213 mmol) and a solution of lithium diisopropylamide (2 M in THF, 160 mL, 320 mmol) and DMPU (41.0 g, 320 mmol) and 2-iodopropane (72.4 g, 426 mmol) in THF (700 mL), ethyl 2-isopropyl-5-methyl-3-methylenehexanoate (28.5 g, 63%) was obtained as a colourless liquid after standard workup and purification by silica-gel flash chromatography (pentane/Et$_2$O, 98:2, R$_f$=0.18). Odour description: agrestic, fruity, balsamic note with ethereal, green facets.

As described for the preparation of 2,5-dimethyl-3-methylenehexan-1-ol (vide supra), from ethyl 2-isopropyl-5-methyl-3-methylenehexanoate (27.2 g, 128 mmol) and LAH (4.86 g, 128 mmol) in THF (450 mL), 2-isopropyl-5-methyl-3-methylenehexan-1-ol (17.2 g, 79%) was obtained as a colourless odoriferous liquid after standard workup and purification by silica-gel flash chromatography (pentane/Et$_2$O, 8:2, R$_f$=0.19). IR (neat): ν=3355 (s, ν O—H), 1465 (w, δ$_{as}$ CH$_3$), 1365 (w, δ$_s$ CH$_3$), 1058 (s, ν C—O), 893 (s, δ C=H) cm$^{-1}$. $^1$H NMR (CDCl$_3$): δ=0.88 (d, J=6.5 Hz, 6H, 1'-Me$_2$), 0.92 (d, J=6.5 Hz, 6H, 5-Me$_2$), 1.65 (br. s, 1H, OH), 1.74-1.80 (m, 2H, 5-, 1'-H), 1.84-1.99 (m, 2H, 4-H$_2$), 1.90-1.93 (m, 1H, 2-H), 3.56-3.64 (m, 2H, 1-H$_2$), 4.88 (d, J=1.0 Hz, 1H, 1'-H$_E$), 4.96 (d, J=1.0 Hz, 1H, 1'-H$_Z$) ppm. $^{13}$C NMR (CDCl$_3$): δ=20.2/21.3 (2q, 1'-Me$_2$), 22.6/22.7 (2q, 5-Me$_2$), 25.5 (d, C-1'), 27.7 (d, C-5), 44.9 (t, C-4), 55.3 (d, C-2), 61.9 (t, C-1), 112.0 (d, C-1"), 148.2 (s, C-3) ppm. MS (EI): m/z (%)=170 (3) [M$^+$], 127 (3) [M$^+$-C$_3$H$_7$], 95 (27) [M$^+$-C$_4$H$_{11}$O], 83 (100) [C$_6$H$_{11}$$^+$], 43 (30) [C$_3$H$_7$$^+$]. Odour description: green-floral fruity note with natural agrestic and woody-earthy, vetiver-type aspects and fruity-aromatic, rhubarb-like facets.

EXAMPLE 6

2-Isopropyl-5,5-dimethyl-3-methylenehexan-1-ol

As described for preparation of ethyl 2,5-dimethyl-3-methylenehexanoate (vide supra), from (E/Z)-ethyl 3,5,5-trimethylhex-2-enoate (40.6 g, 220 mmol) and an LDA solution (2 M in THF, 165 mL, 330 mmol), DMPU (42.3 g, 330 mmol) and 2-iodopropane (74.8 g, 440 mmol) in THF (800 mL), ethyl 2-isopropyl-5,5-dimethyl-3-methylenehexanoate (41.4 g, 83%) was obtained as a colourless liquid after standard workup and purification by silica-gel flash chromatography (pentane/Et$_2$O, 98:2, R$_f$=0.18). Odour description: sweet, fruity note with green aspects.

As described for preparation of 2,5-dimethyl-3-methylenehexan-1-ol (vide supra), from ethyl 2-isopropyl-5,5-dimethyl-3-methylenehexanoate (41.4 g, 183 mmol) and LAH (6.95 g, 183 mmol) in THF (750 mL), 2-isopropyl-5,5-dimethyl-3-methylenehexan-1-ol (28.9 g, 86%) was obtained as a colourless odoriferous liquid after standard workup and purification by silica-gel flash chromatography (pentane/Et$_2$O, 8:2, R$_f$=0.22). IR (neat): ν=3353 (s, ν O—H), 1466 (w, δ$_{as}$ CH$_3$), 1363 (w, δ$_s$, CH$_3$), 1035 (s, ν C—O), 894 (s, δ C=H) cm$^{-1}$. $^1$H NMR (CDCl$_3$): δ=0.92 (d, J=7.0 Hz, 6H, 1'-Me$_2$), 0.95 (s, 9H, 5-Me$_3$) 1.53 (br. s, 1H, OH), 1.79-1.91 (m, 1H, 1'-H), 1.95 (s, 2H, 4-H$_2$), 2.00-2.05 (m, 1H, 2-H), 3.56-3.52 (m, 1H, 1-H$_a$), 3.67-3.73 (m, 1H, 1-H$_b$), 4.92 (d, J=1.0 Hz, 1H, 1'-H$_E$), 5.01 (d, J=1.0 Hz, 1H, 1'-H$_Z$) ppm. $^{13}$C NMR (CDCl$_3$): δ=19.9/21.2 (2q, 1'-Me$_2$), 27.9 (d, C-1'), 30.0 (q, 5-Me$_3$), 31.7 (s, C-5), 50.5 (t, C-4), 54.6 (d, C-2) 61.4 (t, C-1), 113.4 (d, C-1"), 147.4 (s, C-3) ppm. MS (EI): m/z (%)=184 (3) [M$^+$], 154 (2) [M$^+$-CH$_2$O], 83 (22) [C$_6$H$_{11}$$^+$], 57 (100) [C$_4$H$_9$$^+$]. Odour description: pleasant and soft, floral-agrestic note with woody-ambery facets and a musky background.

EXAMPLE 7

Floriental Feminine Fine Fragrance

| Compound/Ingredient | parts by weight 1/1000 |
| --- | --- |
| Agrumex (2-tert-butyl cyclohexyl acetate) | 0.60 |
| Ambrofix ((3aR,5aS,9aS,9bR)-dodecahydro-3a,6,6,9a-tetramethylnaphtho[2,1-b]furan) | 2.00 |
| Benzyl acetate | 0.20 |
| Benzyl salicylate | 0.60 |
| Bourgeonal (3-[4-(1,1-dimethylethyl)phenyl]propanal) | 2.20 |
| Calone 1951 (7-methyl-2H-1,5-benzodioxepin-3(4H)-one) | 0.20 |
| Cashmeran (1,2,3,5,6,7-hexahydro-1,1,2,3,3-pentamethyl-4H-inden-4-one) | 0.07 |
| Cassis Base 345 (Firmenich) | 4.00 |
| Cedarwood oil USA | 0.50 |
| Cedryl methyl ether | 0.30 |
| Cedryl methyl ketone | 1.30 |
| Centifolyl (2-phenylethyl 2,2-dimethylpropanoate) | 0.01 |
| Citron oil Italy | 16.00 |
| Citronellol | 4.00 |
| Coranol (4-cyclohexyl-2-methylbutan-2-ol) | 0.20 |
| Coumarin crystalline | 0.01 |
| alpha-Damascone | 0.40 |
| beta-Damascone | 0.01 |
| gamma-Decalactone | 3.50 |
| beta-Dihydroionone | 0.03 |
| Dihydromyrcenol | 0.20 |
| 3,7-Dimethylocta-1,6-diene-3-yl dimethylcarbamate | 10.00 |
| Dipropylene glycol (DPG) | 15.67 |
| Ethyl acetoacetate | 6.00 |
| Ethylene brassylate (1,4-dioxacycloheptadecane-5,17-dione) | 200.00 |
| Ethyl linalool | 65.00 |
| Ethyl safranate | 0.05 |
| Ethyl vanillin | 0.05 |
| Eugenol | 0.04 |
| Fennaldehyde (3-(4-methoxyphenyl)-2-methylpropanal) | 0.10 |
| Florol (2-isobutyl-4-methyltetrahydro-2H-pyran-4-ol) | 0.40 |
| Fructone (ethyl 2-methyl-1,3-dioxolane-2-acetate) | 0.01 |
| Gardenol (1-phenylethyl acetate) | 0.03 |
| Georgywood (cis-1-(1,2,3,4,5,6,7,8-octahydro-1,2,8,8-tetramethyl-2-naphthalenyl)ethanone) | 5.00 |
| Geranium oil Egypt | 2.00 |
| Ginger CO$_2$ extract | 1.00 |
| Hedione (methyl dihydrojasmonate) | 440.00 |
| Heliotropine crystalline | 0.05 |
| (2E)-Hex-2-enal @ 10% TEC (triethyl citrate) | 1.40 |
| (3Z)-Hex-3-enol | 2.00 |
| (3Z)-Hex-3-enyl acetate | 1.50 |
| (3Z)-Hex-3-enyl methyl carbonate | 3.00 |
| alpha-Hexylcinnamaldehyde | 0.90 |
| beta-Ionone | 0.01 |
| Indol @ 1% TEC | 1.00 |
| Isoamyl acetate | 0.01 |
| Iso-E-Super (2,3,8,8-tetramethyl-1,2,3,4,5,6,7,8-octahydro-2-naphthalenyl methyl ketone and isomers) | 130.00 |
| Isoraldeine 95 (iso-methyl alpha-ionone) | 6.00 |
| Jasmine absolute sambac | 1.00 |
| cis-Jasmone | 0.01 |
| Linalool | 3.50 |
| Linalyl acetate | 4.00 |
| Lilial (2-methyl-3-(4-tert-butylphenyl)propanal) | 3.50 |
| Magnolan (4,4a,5,9b-tetrahydro-2,4-dimethylindeno[1,2-d]-1,3-dioxin) | 2.50 |
| Maltol @ 1% TEC | 1.00 |
| Manzanate (ethyl 2-methylpentanoate) | 0.10 |
| 2-Methoxy-4-propenylphenylacetate | 0.01 |
| Methyl anthranilate | 0.01 |
| Methyl N-methylanthranilate | 0.02 |

| Compound/Ingredient | parts by weight 1/1000 |
|---|---|
| Methyl pamplemousse (6,6-dimethoxy-2,5,5-trimethylhex-2-ene) | 0.02 |
| Muscenone (3-methylcyclopentadec-4/5-enone) | 10.00 |
| 1-(2-Naphthalenyl)ethanone | 0.01 |
| Nerolidol | 8.00 |
| gamma-Nonalactone | 0.08 |
| Patchouli oil Indonesia w/o iron | 0.50 |
| 15-Pentadecanolide | 5.00 |
| Phenoxanol (3-methyl-5-phenylpentanol) | 2.20 |
| 2-Phenylethyl acetate | 0.01 |
| 2-Phenylethyl alcohol | 0.20 |
| 2-Phenylethyl phenylacetate | 0.20 |
| Pink pepper CO$_2$ extract (Shinus molle) | 2.00 |
| Radjanol (2-ethyl-4-(2,2,3-trimethyl-3-cyclopenten-1-yl)but-2-en-1-ol) | 0.05 |
| Rose absolute | 0.20 |
| Rose oxide | 0.02 |
| Terpineol | 0.20 |
| Tricyclal (2,4-dimethylcyclohex-3-ene-1-carboxaldehyde) | 1.30 |
| 2,2,5-Trimethyl-5-pentylcyclopentanone | 0.30 |
| Tropional (3-(benzo[d][1,3]dioxol-5-yl)-2-methylpropanal) | 13.50 |
| gamma-Undecalactone | 2.00 |
| Undecavertol (4-methyldec-3-en-5-ol) | 0.80 |
| Vanillin | 0.20 |
| Viridine (2,2-dimethoxyethyl benzene) | 0.01 |
| 2,5-Dimethyl-3-methylenehexan-1-ol | 10.00 |
| | 1000 |

At only 1%, 2,5-dimethyl-3-methylenehexan-1-ol conveys to the top note of this complex and yet well-balanced floriental feminine fine fragrance a very natural and pleasant green, floral-rosy signature that harmonies extremely well with the peachy, hesperidic, flowery-fresh agrestic accord around ethyl linalool, allowing sparkling green-natural lily-of-the-valley facets to glimmer through. Besides, 2,5-dimethyl-3-methylenehexan-1-ol carries the composition from the top to the floral rosy heart with its luscious hyacinth character that plays in the main theme of the perfume with a bouquet of rose oil, jasmine, and lily-of-the-valley while it pushes the strength and the character of this floral composition. The scent then finishes into an oriental woody-balsamic, vanillin-laden fond that with its heavy even somewhat dark character emphasizes the delicacy of the rose that, thanks to the very special character of 2,5-dimethyl-3-methylenehexan-1-ol, remains in every facet new, fresh and unprecedented though it is so exuberantly presented.

EXAMPLE 8

'Green Tea' Fragrance for Cosmetic Formulations

| Compound/Ingredient | parts by weight 1/460 |
|---|---|
| n-Allyl alpha-ionone | 1.50 |
| Ambroxan ((3aR,5aS,9aS,9bR)-dodecahydro-3a,6,6,9a-tetramethylnaphtho[2,1-b]furan) | 2.00 |
| Bergamot oil Italy w/o bergaptene | 49.00 |
| Black pepper oil | 0.50 |
| Cardamom seed oil | 3.00 |
| Cedryl acetate crystalline | 0.60 |
| Citron oil Italy | 1.50 |
| Citronellol | 12.00 |
| Clary sage oil France | 3.00 |
| beta-Damascenone | 0.30 |
| Dipropylene glycol (DPG) | 30.18 |
| Ethylene brassylate (1,4-dioxacycloheptadecane-5,17-dione) | 26.00 |
| Evernyl (methyl 2,4-dihydroxy-3,6-dimethylbenzoate) | 0.80 |
| Geranyl acetate | 2.00 |
| Habanolide (oxacyclohexadec-12-en-2-one) | 3.00 |
| Hedione (methyl dihydrojasmonate) | 126.00 |
| Hedione high-cis ((Z)-methyl dihydrojasmonate) | 90.00 |
| (3Z)-Hex-3-enyl acetate | 0.03 |
| beta-Ionone | 10.00 |
| Iso E Super (2,3,8,8-tetramethyl-1,2,3,4,5,6,7,8-octahydro-2-naphthalenyl methyl ketone and isomers) | 20.00 |
| Linalool | 21.00 |
| Mandarin oil yellow | 8.00 |
| Nutmeg oil Indonesia | 4.00 |
| Orange oil Florida | 24.00 |
| 2-Phenylethyl acetate | 4.00 |
| 2-Phenylethyl phenylacetate | 5.00 |
| 2-Phenylethanol | 1.00 |
| Tricyclal (2,4-dimethylcyclohex-3-ene-1-carboxaldehyde) | 1.50 |
| gamma-Undecalactone | 0.09 |
| 2,5-Dimethyl-3-methylenehexan-1-ol | 10.00 |
| | 460.00 |

At less than 2.5%, 2,5-dimethyl-3-methylenehexan-1-ol conveys to this 'Green Tea' fragrance for cosmetic formulations a special green-floral signature that enriches the 'green tea' theme with "vert de lilas" facets reminiscent of lilac, hyacinth and peony, greatly increases the strength, and with its slightly agrestic-earthy aspects the natural character of the composition. In addition, this new green-floral odorant provides lift and a comforting character, which emphasizes functional skin-caring properties of a given cosmetic formulation.

The invention claimed is:

1. A compound of formula I,

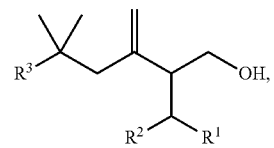

in which $R^1$ and $R^2$ are selected from H or Me and $R^3$ is selected from H, Me and Et.

2. A compound according to claim 1 selected from the group consisting of:
2,5-dimethyl-3-methylenehexan-1-ol,
2,5,5-trimethyl-3-methylenehexan-1-ol,
2-ethyl-5-methyl-3-methylenehexan-1-ol,
2-ethyl-5,5-dimethyl-3-methylenehexan-1-ol,
2-isopropyl-5-methyl-3-methylenehexan-1-ol, and
2-isopropyl-5,5-dimethyl-3-methylenehexan-1-ol.

3. A fragrance application comprising
a) at least one compound of formula I as defined in claim 1; and
b) a consumer product base.

4. A fragrance application according to claim 3 wherein the product base is selected from the group consisting of: fine fragrance product, household product, laundry product, body care product and cosmetic product.

5. A fragrance composition comprising a compound of formula I as defined in claim 1.

6. A method of improving, enhancing or modifying a perfume composition or fragrance application comprising the step of: incorporating an effective amount of a one compound of formula I as defined in claim 1 to a base material.

* * * * *